(12) United States Patent
Hesselroth et al.

(10) Patent No.: US 7,716,999 B2
(45) Date of Patent: May 18, 2010

(54) TEST METHOD FOR DETERMINING MICROSTRUCTURE DEFORMATION RESISTANCE OF A MICROSTRUCTURED FILM

(75) Inventors: Adam H. Hesselroth, Hudson, WI (US); Stephen J Dreyer, North St. Paul, MN (US); Mark R. Dupre, Oakdale, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 55 days.

(21) Appl. No.: 12/245,046

(22) Filed: Oct. 3, 2008

(65) Prior Publication Data

US 2009/0107261 A1 Apr. 30, 2009

Related U.S. Application Data

(60) Provisional application No. 60/983,943, filed on Oct. 31, 2007.

(51) Int. Cl.
 *G01L 1/04* (2006.01)
(52) U.S. Cl. .................................. 73/862.621
(58) Field of Classification Search ............... 73/777, 73/862.621
 See application file for complete search history.

(56) References Cited

U.S. PATENT DOCUMENTS

| | | | |
|---|---|---|---|
| 5,626,800 A | 5/1997 | Williams et al. | |
| 6,781,702 B2 * | 8/2004 | Giannakopoulos et al. | .. 356/601 |
| 7,074,463 B2 * | 7/2006 | Jones et al. | ..... 428/1.1 |
| 7,282,272 B2 * | 10/2007 | Jones et al. | ..... 428/500 |
| 7,568,396 B2 * | 8/2009 | He et al. | ........ 73/777 |
| 2006/0030062 A1 * | 2/2006 | He et al. | ........ 438/18 |
| 2009/0281768 A1 * | 11/2009 | Fitzgerald et al. | ....... 702/181 |

* cited by examiner

*Primary Examiner*—Lisa M Caputo
*Assistant Examiner*—Freddie Kirkland, III
(74) *Attorney, Agent, or Firm*—Carolyn A. Fischer

(57) ABSTRACT

Test method for determining (e.g. prism) microstructure deformation of a microstructured (e.g. brightness enhancing) film are described.

19 Claims, 1 Drawing Sheet

U.S. 7,716,999 B2

TEST METHOD FOR DETERMINING MICROSTRUCTURE DEFORMATION RESISTANCE OF A MICROSTRUCTURED FILM

RELATED APPLICATION DATA

This application claims the benefit of U.S. Provisional Application Ser. No. 60/983,943, filed Oct. 31, 2007.

BACKGROUND

Groove tip impression is deformation of the prism tips (i.e. apexes) of prismatic microstructures of a brightness enhancement film. U.S. Pat. No. 5,626,800 describes methods of producing a microstructure bearing article such as a brightness enhancing films. Also described is a groove tip penetration test having good correlation to visible groove tip impressions. However, since the groove tip penetration test described in U.S. Pat. No. 5,626,800 requires the use of special equipment to measure the penetration of steel balls into a brightness enhancement film, industry would find advantage in alternative methods of determining resistance to groove tip impression.

SUMMARY

Presently described are methods of determining microstructure deformation of a microstructured film. The method comprises providing a uniformly distributed pressure on at least one microstructured film test sample; conditioning the microstructured film at an elevated temperature (e.g. above 25° C.); removing the uniformly distributed pressure; and determining the magnitude of deformation of the microstructured surface.

The method is particularly useful for screening various polymerizable resin compositions for their suitability for use as (e.g. prism) microstructures of a (e.g. brightness enhancing) microstructured film.

DETAILED DESCRIPTION OF PREFERRED EMBODIMENTS

Figure 1:
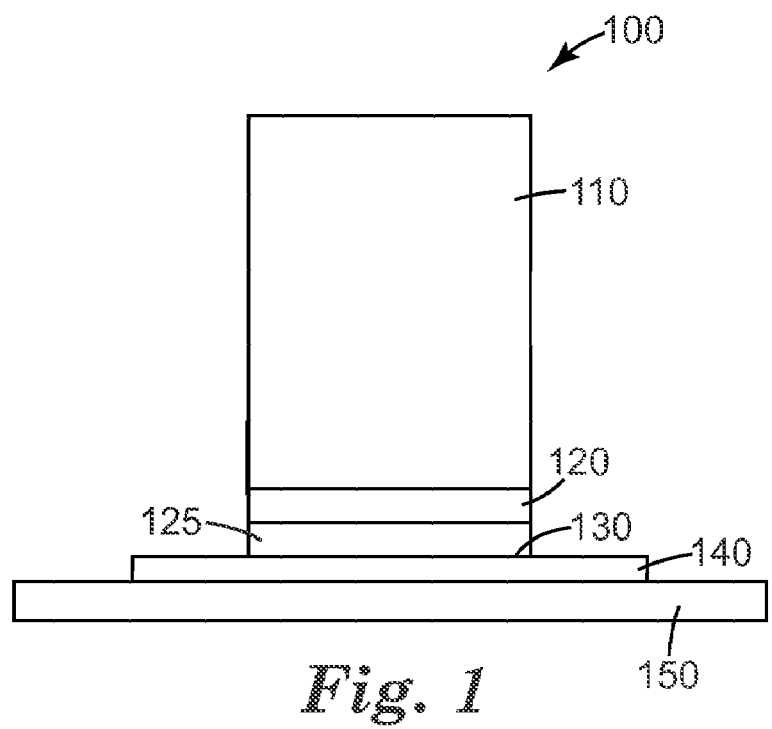
FIG. 1 is a schematic cross-section of an embodied assembly for providing a uniformly distributed pressure on a microstructured film or stack of films.

Presently described are test methods for determining microstructure deformation of a microstructured film. The invention will be described with respect to determining "groove tip impression" of a microstructured film having prismatic microstructures such as a brightness enhancing films. However, the test method herein is suitable for other shaped microstructures, particularly those prepared as a roll-good from polymeric materials.

The term "microstructure" is used herein as defined and explained in U.S. Pat. No. 4,576,850. Thus, it means the configuration of a surface that depicts or characterizes the predetermined desired utilitarian purpose or function of the article having the microstructure. Discontinuities such as projections and indentations in the surface of said article will deviate in profile from the average center line drawn through the microstructure such that the sum of the areas embraced by the surface profile above the center line is equal to the sum of the areas below the line, said line being essentially parallel to the nominal surface (bearing the microstructure) of the article. The heights of said deviations will typically be about +/−0.005 to +/−750 microns, as measured by an optical or electron microscope, through a representative characteristic length of the surface, e.g., 1-30 cm. Said average center line can be piano, concave, convex, aspheric or combinations thereof. Articles where said deviations are of low order, e.g., from +/−0.005 +/−0.1 or, preferably, +/−0.05 microns, and said deviations are of infrequent or minimal occurrence, i.e., the surface is free of any significant discontinuities, are those where the microstructure-bearing surface is an essentially "flat" or "smooth" surface, such articles being useful, for example, as precision optical elements or elements with a precision optical interface, such as ophthalmic lenses. Articles where said deviations are of low order and of frequent occurrence include those having anti-reflective microstructure. Articles where said deviations are of high-order, e.g., from +/−0.1 to +/−750 microns, and attributable to microstructure comprising a plurality of utilitarian discontinuities which are the same or different and spaced apart or contiguous in a random or ordered manner, are articles such as retroreflective cube-corner sheeting, linear Fresnel lenses, video discs and brightness enhancing films. The microstructure-bearing surface can contain utilitarian discontinuities of both said low and high orders. The microstructure-bearing surface may contain extraneous or non-utilitarian discontinuities so long as the amounts or types thereof do not significantly interfere with or adversely affect the predetermined desired utilities of said articles.

For microstructured optical films, the resin composition and thus the solidified microstructures are light-transmissive. Exemplary microstructured optical films include brightness enhancing films, retroreflective sheeting, light-collimating (e.g. privacy films), and sheet molds suitable for molding (e.g. plasma) display panels.

Microstructured optical articles are commonly prepared by contacting a moldable resin composition with a microstructured tool. Once solidified, the microstructures comprise a relatively hard polymeric material. The polymeric composition may be thermoplastic, yet is preferably a reaction product of a (e.g. ultraviolet) polymerizable resin. The elastic modulus of the composition of the microstructures is typically greater than $16 \times 10^8$ pascals, preferably greater than $18 \times 10^8$ pascals, and more preferably is greater than $25 \times 10^8$ pascals. The term "elastic modulus" as used herein means the elastic modulus determined according to ASTM D882-75b using Static Weighing Method A with a 12.5 centimeter (5 inch) initial grip separation, a 2.5 centimeter (1 inch) sample width, and a 2.5 centimeter/minute (1 inch/minute) rate of grip separation.

Various resin compositions suitable for the preparation of the microstructures of a brightness enhancing film are known such as described in US2006/0004166, U.S. Patent No. WO 2006/007286, and US2006/0204676. In some embodiments, the resin composition further comprises inorganic nanoparticles such as silica, zirconia, titania, antimony oxides, alumina, tin oxides, mixed metal oxides thereof, and mixtures thereof. The refractive index of the organic component as well as the polymerizable composition has a refractive index of at least 1.47. The refractive index of the organic component or the polymerizable composition may be at least 1.48, 1.49, 1.50, 1.51, 1.52, 1.53, 1.54, 1.55, 1.56, 1.57, 1.58, 1.59, or 1.60. The polymerizable composition including the nanoparticles can have a refractive index as high as 1.70. (e.g. at least 1.61, 1.62, 1.63, 164, 1.65, 1.66, 1.67, 1.68, or 1.69) High transmittance in the visible light spectrum is also typically preferred.

As described in Lu, U.S. Pat. No. 5,183,597 and Lu et al., U.S. Pat. No. 5,175,030, a microstructure-bearing article (e.g. brightness enhancing film) can be prepared by a method including the steps of (a) preparing a polymerizable composition (i.e. the polymerizable composition of the invention); (b) depositing the polymerizable composition onto a master negative microstructured molding surface in an amount barely sufficient to fill the cavities of the master; (c) filling the cavities by moving a bead of the polymerizable composition between a preformed base and the master, at least one of which is flexible; and (d) curing the composition. The master can be metallic, such as nickel, nickel-plated copper or brass, or can be a thermoplastic material that is stable under the polymerization conditions, and that preferably has a surface energy that allows clean removal of the polymerized material from the master. One or more the surfaces of the base film can be optionally be primed or otherwise be treated to promote adhesion of the optical layer to the base.

The particular chemical composition and thickness of the base material for any optical product can depend on the requirements of the particular optical product that is being constructed. That is, balancing the needs for strength, clarity, temperature resistance, surface energy, adherence to the optical layer, among others. The thickness of the base layer is typically at least about 0.025 millimeters (mm) and more typically at least about 0.25 mm. Further, the base layer generally has a thickness of no more than about 1 mm.

Useful base layer materials include cellulose acetate butyrate, cellulose acetate propionate, cellulose triacetate, polyether sulfone, polymethyl methacrylate, polyurethane, polyester, polycarbonate, polyvinyl chloride, syndiotactic polystyrene, polyethylene naphthalate, copolymers or blends based on naphthalene dicarboxylic acids, and glass. Optionally, the base material can contain mixtures or combinations of these materials. For example, the base may be multi-layered or may contain a dispersed phase suspended or dispersed in a continuous phase. Exemplary base layer materials include polyethylene terephthalate (PET) and polycarbonate. Examples of useful PET films include photograde polyethylene terephthalate (PET) and PET commercially available from DuPont Films of Wilmington, Del., under the trade designation "Melinex".

The base layer material can be optically active, and can act as a polarizing material. A number of base layer materials are known to be useful as polarizing materials. Polarization of light through a film can be accomplished, for example, by the inclusion of dichroic polarizers in a film material that selectively absorbs passing light. Light polarization can also be achieved by including inorganic materials such as aligned mica chips or by a discontinuous phase dispersed within a continuous film, such as droplets of light modulating liquid crystals dispersed within a continuous film. As an alternative, a film can be prepared from microfine layers of different materials. The polarizing materials within the film can be aligned into a polarizing orientation, for example, by employing methods such as stretching the film, applying electric or magnetic fields, and coating techniques.

Brightness enhancing films are known. For example, various brightness enhancing films are depicted in U.S. Pat. No. 7,074,463; incorporated herein by reference. A brightness enhancing film generally includes a linear array of regular right prisms. By right prisms, it is meant that the apex angle (i.e. the groove tip) is approximately 90°, but can also range from approximately 70° to 120° or from approximately 80° to 100°. The apex may be sharp, rounded, fattened, or truncated. The prism facets need not be identical, and the prisms may be tilted with respect to each other. Furthermore, the relationship between the thickness of the film and the height of the prisms can vary. However, it is desirable to use thinner films with well defined prism facets.

The method of determining microstructure deformation of a microstructured film or groove tip impression of a prismatic microstructured film comprises providing a uniformly distributed pressure on at least one sample of a microstructured film. It is typically preferred to concurrently test several samples, by providing a uniformly distributed pressure on a stack of microstructured films. The number of films in the stack is typically at least 2, 3, 4, or 5 and usually no greater than about 25 (e.g. for microstructured films having a thickness of about 1 mil). For thicker films, the stack typically has 5 to 10 films.

One suitable assembly 100 for providing a uniformly distributed pressure is depicted in FIG. 1. A mass 110 is disposed upon a microstructured film 140 or stack of microstructured films. Various shaped masses of various weights could be employed. The pressure is selected based on the relative hardness of the microstructured surface being tested. For flexible microstructures, the pressure may be as low as 0.25 lb/in$^2$ or 0.50 lb/in$^2$. For harder microstructures however, the pressure may be as high as 5 lb/in$^2$. For many microstructured surfaces prepared from the reaction product of a polymerizable resin composition, a suitable pressure typically ranges from about 1 to 2 lb/in$^2$. Such a pressure can be obtained with a cylindrical 12 kg mass having a diameter of 4.5" (surface area of 15.90 in$^2$) providing a pressure of 1.66 lb/in$^2$.

Since the contacting surface of standard laboratory masses is not perfectly smooth, it is preferred to provide one or more compressible materials 120 and 125 between the mass and the microstructured film(s) to avoid single points of contact between the mass and the film(s). In one embodiment, a relatively hard foam tape 120 is adhered to cover the contacting surface of the mass. By relatively hard foam (e.g. tape), it is meant that the foam tape substantially maintains its thickness when bearing the weight of the mass. One exemplary hard double-faced foam (density of 200-275 kg/m$^2$) tape is commercially available from 3M Company under the trade designation "1 Wide Hard Foam Tape—⅛" Thick Scotch Double Sided Foam Tape—4008". The hard foam tape provides the bulk pressure distribution of the mass. An optional soft foam (e.g. tape) 125 that compresses in thickness when bearing the weight of the mass is then adhered to the hard foam tape. One exemplary soft double-faced foam tape is commercially available from 3M Company under the trade designation "1" Wide Soft Foam Tape—Scotch Mounting Tape—4012". The purpose of the soft foam tape is to mask any dirt or contaminants on the film surface. An optional non-tacky polymeric material 130 such an 10 mil Teflon P.T.F.E. commercially available from McMaster-Carr, Part Number 8569K41 can then be adhered to the soft foam tape to prevent the opposing adhesive surface of the double-faced soft foam tape from contacting and adhering to the surface of the microstructured film test sample and also to cover the seam between the adjacent pieces of hard foam tape.

As an alternative to providing one or more compressible materials between the mass and the microstructured film(s), the contacting surface of the mass could be machined to provide a sufficiently planar surface. The mass could then directly contact the microstructured film providing a uniformly distributed pressure or be used with only the soft foam.

Once the uniformly distributed pressure has been provided on the microstructured film or stack of films, the assembly is conditioned at a temperature above room temperature. The temperature typically ranges from about 30 deg. C. to about 40 deg. C. Even higher temperatures may be suitable such as for embodiments wherein the microstructured surface is prepared from a resin composition comprising a high glass transition temperature (Tg). The conditioning is typically done by placing the assembly of FIG. 1 in a temperature controlled chamber such as a standard laboratory convection oven. Other temperature controlled chambers could be used provided a constant temperature +/−2 deg. C. can be maintained uniformly throughout the chamber. It is preferred that a constant temperature is maintained to +/−1 deg. C., and more preferably +/−0.5 deg. C., particularly when the glass transition temperature (Tg) of the composition of the microstructures is within 10 deg. C. of the conditioning temperature of the test sample(s).

When the microstructured film is formed into a roll-good, the temperature particularly at the core of the roll can reach up to 30 deg. C. Further, when transported, the temperature of a roll of microstructured film can reach as high as 40 deg. C., particularly in warm climates. Hence, room temperature testing can be inadequate since such temperature does not correlate well to the actual conditions the microstructured film may encounter that would result in groove tip impressions. In addition, since elevating the temperature tends to accelerate the formation of groove tip impression, increasing the temperature can shorten the duration of the test, thereby providing test results sooner. This is particularly useful for screening resin compositions for their suitability for use as microstructures of a microstructured film. In combination with increasing the temperature, faster results could also be obtained by increasing the pressure.

After conditioning, the method comprises removing the uniformly distributed pressure from the microstructured film sample and determining the magnitude of deformation of the microstructured surface.

Figure 2:
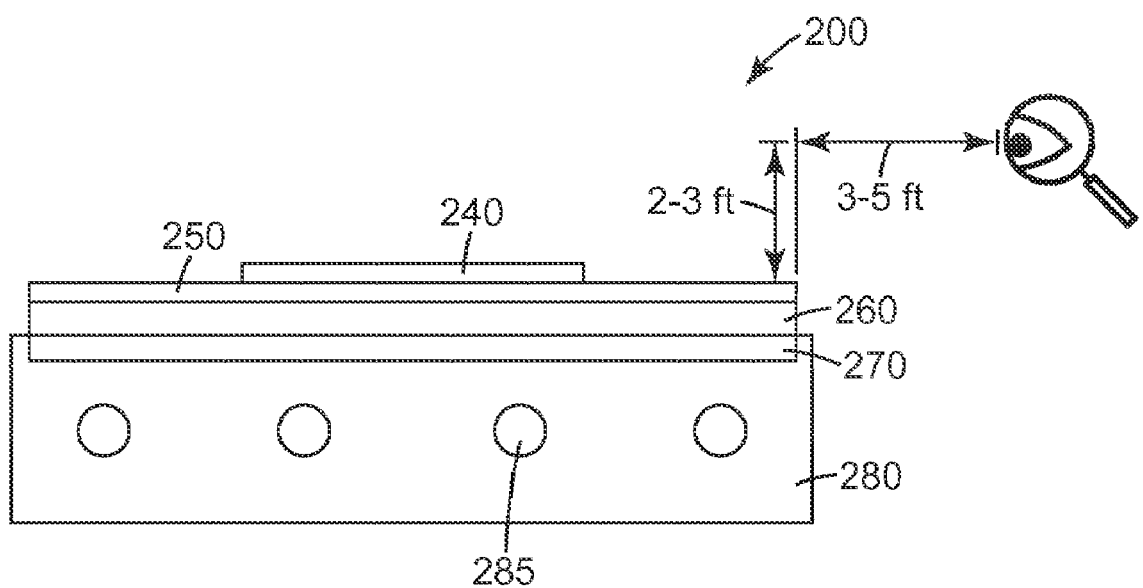
FIG. 2 is a schematic cross-section of an embodied assembly for inspecting a sample for visible groove tip impression.

One way of determining the magnitude of groove tip impression is to rate the deformation based on visual inspection. With reference to FIG. 2, an illuminated table 200 may be employed to inspect the microstructured films for groove tip impression. In one embodiment, the illuminated table 200 includes a light box 280, having (e.g. fluorescent) bulbs 285 and a diffuser plate 270 above the bulbs to diffuse and thereby provide a uniformly lighted surface. A piece of brightness enhancing film 260 commercially available from 3M Company, St. Paul, Minn. under the trade designation "BEF II 90/50" is provided above the diffuser. The purpose of the brightness enhancing film is to enhance the brightness of the groove tip impression so it is easier to visually detect. A protective sheet 250 such as a sheet of ¼" inch thick (e.g. transparent window) glass is typically provided above the brightness enhancing film. A microstructured film test sample 240 that has been subjected to elevated temperature and pressure is positioned on the protective sheet for visible inspection of the presence of microstructure deformation such as groove tip impression. The test sample is positioned such that the prisms are facing up and are aligned orthoganol to the direction of the prisms of the brightness enhancing film of the illuminated table. It is typically preferred to inspect the samples in a side by side comparison relative to each other, or even more preferably relative to "standards" having a specific magnitude of groove tip impression. The groove tip impression appears as a white circle (i.e. since a circular contacting surface mass was used) on the microstructured film sample. As the magnitude of the groove tip impression increases, the white circle becomes brighter and more visible. One suitable rating scale is as follows:

| Rating | Description |
|--------|-------------|
| 0 | No groove tip impression (GTI), no circle |
| 1 | GTI is barely visible, patchy outline of circle is visible |
| 2 | GTI is visible but very light, circle is visible but dim |
| 3 | GTI is moderate, clearly defined circle |
| 4 | GTI is heavy, clearly defined bright circle |
| 5 | GTI is "maxed out", circle with maximum brightness (GTI unable to become worse) |

EXAMPLES

A representative polymerizable composition (Composition 1) containing 65% of a first monomer comprising a major portion of 2-propenoic acid, (1-methylethylidene)bis[(2,6-dibromo-4,1-phenylene)oxy(2-hydroxy-3,1-propanediyl)] ester, 25% phenoxy ethyl acrylate, and 10% trimethylolpropane triacrylate was prepared. A second polymerizable composition (Composition 2), described as "B", in the Table at column 8 of U.S. Pat. No. 5,626,800 was also prepared. To both polymerizable resin samples was added 0.1 pph of a photoinitiator commercially available from BASF Charlotte, N.C. under the trade designation "Lucirin TPO" and 0.35 pph of a photoinitiator commercially available from Ciba Specialty Chemicals "Darocure 1173". The compositions were prepared into brightness enhancing film by depositing the polymerizable resin composition onto a microstructured tool filling the cavities of the tool and curing the polymerizable composition between a preformed (PET) base and the tool using the same process conditions.

The resulting brightness enhancing films were tested for Groove Tip Impression utilizing the assembly depicted in FIG. 1. Specifically, the test was conducted using the following steps:

1. Each brightness enhancing film was cut into test samples having the approximate dimensions of 8"×9".
2. The top side of a glass panel having dimensions of about 10"×10" was cleaned with glass cleaner.
3. Fifteen samples of brightness enhancing film were placed on top of the protective glass panel of the illuminated table. All samples were placed (e.g. prism) microstructured surface side down with the prisms running the same direction sample to sample.
4. The glass panel having the film samples was placed in a convection environmental oven equilibrate to 40° C. dry heat, having a humidity of 20% RH or lower.
5. A mass having the hard foam tape, soft foam tape, and Teflon cover sheet (as previously described with respect to FIG. 1) was placed on the center of film stack.
6. The assembly was conditioned in the oven for a specified duration of time (e.g. 40 or 60) minutes.
7. The mass was removed from the test samples and within 5 days after removal of the mass the magnitude of deformation was determined using the assembly of FIG. 2 and the rating scale previously described. In this particular experiment, only the middle 5 samples were evaluated for groove tip impression to most closely model films in a roll which are contacted with film on both sides.

In one set of experiments, the Groove Tip Impression was tested after being conditioned for 40 minutes at 40 deg. C. The brightness enhancing film prepared from representative Composition 1 exhibited no (i.e. "0" according to rating scale) groove tip impressions; whereas the brightness enhancing film prepared from Composition 2 exhibited a groove tip impression rating of 4-5. These results demonstrate that microstructures prepared from Composition 1 had better resistance to groove tip impressions relative to Composition 2.

In a second set of experiments, both brightness enhancing films were subjected to post-cure heat treatment for 1 minute at a temperature of 80 deg. C. The Groove Tip Impression was tested after being conditioned for 60 minutes at 40 deg. C. The brightness enhancing film prepared from Composition 1 exhibited no (i.e. "0" according to rating scale) groove tip impressions whereas the brightness enhancing film prepared from Composition 2 exhibited a groove tip impression rating of 4-5.

What is claimed is:

1. A method of determining microstructure deformation resistance of a microstructured film comprising:
providing a uniformly distributed pressure on at least one test sample of a microstructured film, the microstructured film having a microstructured surface;
conditioning the microstructured film test sample having the uniformly distributed pressure at a temperature above 25° C.;
removing the uniformly distributed pressure from the microstructured film test sample; and
determining the magnitude of deformation of the microstructured surface of the microstructured film test sample.

2. The method of claim 1 wherein the microstructured surface comprises prism structures.

3. The method of claim 2 wherein the microstructured film test sample is a brightness enhancing film.

4. The method of claim 1 wherein a uniformly distributed pressure is provided on a stack of microstructured films.

5. The method of claim 4 wherein the stack comprises 2 to 20 films.

6. The method of claim 4 wherein the microstructured surface of the microstructured film test samples of the stack comprise prism structures substantially parallel to each other and the prisms structures of the stack are aligned in the same direction.

7. The method of claim 4 wherein the microstructured film test samples have an opposing surface that is substantially planar and the films of the stack are assembled such that the microstructured surface of a first film contacts the opposing surface of an adjacent film.

8. The method of claim 1 wherein the uniformly distributed pressure is provided by a mass disposed upon the microstructured film or a stack of microstructured films.

9. The method of claim 8 wherein the microstructured film has an opposing surface that is substantially planar and the mass is disposed upon the substantially planar surface.

10. The method of claim 8 wherein at least one compressible material is provided between the mass and the microstructured film or stack of microstructured films.

11. The method of claim 10 wherein the compressible material comprises a hard foam.

12. The method of claim 1 wherein the temperature ranges from 30° C. to 40° C.

13. The method of claim 1 wherein the pressure ranges from about 0.25 to 5 lb/in$^2$.

14. The method of claim 1 wherein the pressure ranges from about 1 to 2 lb/in$^2$.

15. The method of claim 1 wherein the magnitude of deformation of the microstructured surface is determined by rating the deformation based on visual inspection.

16. The method of claim 15 wherein the microstructured film is placed on an illuminated table.

17. The method of claim 16 wherein the illuminated table comprises a brightness enhancing film having linear prisms.

18. The method of claim 17 wherein the microstructured film test sample is a brightness enhancing film having linear prisms and the prisms of the microstructured film test sample are aligned orthogonal to the prisms of the brightness enhancing film of the illuminated table.

19. The method of claim 1 wherein the microstructured film comprise microstructures prepared from a solidified polymeric material having an elastic modulus greater than $16 \times 10^8$ pascals.

* * * * *